US009437411B2

(12) United States Patent
Chartier et al.

(10) Patent No.: US 9,437,411 B2
(45) Date of Patent: Sep. 6, 2016

(54) MULTI-ELEMENT ISOTOPIC MEASUREMENT BY DIRECT COUPLING OF A MULTI-CYCLE ISOTACHOPHORESIS TECHNIQUE AND A MASS SPECTROMETRY TECHNIQUE

(71) Applicant: COMMISSARIAT A L'ENERGIE ATOMIQUE ET AUX ENERGIES ALTERNATIVES (CEA), Paris (FR)

(72) Inventors: Frédéric Chartier, Fontenay-aux-Roses (FR); Laurent Vio, Dagneux (FR); Anthony Nonell, Longjumeau (FR); Hélène Isnard, Antony (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 0 days.

(21) Appl. No.: 14/977,584

(22) Filed: Dec. 21, 2015

(65) Prior Publication Data

US 2016/0181081 A1  Jun. 23, 2016

(30) Foreign Application Priority Data

Dec. 22, 2014  (FR) .................................... 14 63134

(51) Int. Cl.
*G01N 27/447*    (2006.01)
*G01N 27/26*    (2006.01)
(Continued)

(52) U.S. Cl.
CPC ............. *H01J 49/105* (2013.01); *B01D 59/42* (2013.01); *G01N 27/44765* (2013.01); *G01N 27/44773* (2013.01); *G01N 27/622* (2013.01); *H01J 49/0031* (2013.01)

(58) Field of Classification Search
CPC ........... B01L 3/502753; B01L 3/5027; G01N 27/44743; G01N 27/44773; G01N 27/44791; G01N 27/447; G01N 27/44704; G01N 27/44717; G01N 27/44721; G01N 27/44756; G01N 27/44765; G01N 27/622; G01N 1/40; G01N 30/00; H01J 49/0031; H01J 49/167
USPC ........ 250/282, 283, 288; 204/421, 601, 453, 204/549, 600, 454, 542, 554, 645
See application file for complete search history.

(56) References Cited

U.S. PATENT DOCUMENTS 3,705,845 A     12/1972  Everaerts
5,942,093 A *   8/1999   Rakestraw ....... G01N 27/44704
                                                    204/450
(Continued)

FOREIGN PATENT DOCUMENTS

WO     2012/072963 A1    6/2012

OTHER PUBLICATIONS

F. M. Everaerts et al., "Isotachophoresis: Experiments with Electrolyte Counterflow," Journal of Chromatography 60, 1971, pp. 397-405.

(Continued)

*Primary Examiner* — David A Vanore
(74) *Attorney, Agent, or Firm* — Baker & Hostetler LLP

(57) ABSTRACT

A method for separating electrically charged species contained in a solution by an isotachophoresis method applied in an electrophoresis device, the isotachophoresis method being coupled to isotopic measurement using a mass spectrometer. The method notably comprises a step of stopping the voltage applied to the terminal of the electrophoresis capillary and transient application of a counter-pressure making it possible to utilize the length of the capillary several times and extend the separation distance artificially.

11 Claims, 14 Drawing Sheets

(51) Int. Cl.
*B01D 57/02* (2006.01)
*H01J 49/10* (2006.01)
*H01J 49/00* (2006.01)
*B01D 59/42* (2006.01)
*G01N 27/62* (2006.01)

(56) References Cited

U.S. PATENT DOCUMENTS

| | | | |
|---|---|---|---|
| 6,428,666 B1 * | 8/2002 | Singh | B01J 4/04 |
| | | | 204/450 |
| 7,160,423 B2 * | 1/2007 | Chien | B01F 13/0076 |
| | | | 204/451 |
| 9,110,016 B2 * | 8/2015 | Chartier | H01J 49/105 |
| 2002/0079223 A1 * | 6/2002 | Williams | B01L 3/5027 |
| | | | 204/549 |
| 2004/0060821 A1 * | 4/2004 | Williams | B01L 3/5027 |
| | | | 204/549 |
| 2016/0084805 A1 * | 3/2016 | Kelly | G01N 30/08 |
| | | | 204/451 |
| 2016/0181081 A1 * | 6/2016 | Chartier | H01J 49/105 |
| | | | 250/283 |

OTHER PUBLICATIONS

A. Pitois et al., Determination of fission products in nuclear samples by capillary electrophoresis-inductively coupled plasma mass spectrometry (CE-ICP-MS), Science Direct, International Journal of Mass Spectrometry 270, 2008, pp. 118-126.

* cited by examiner

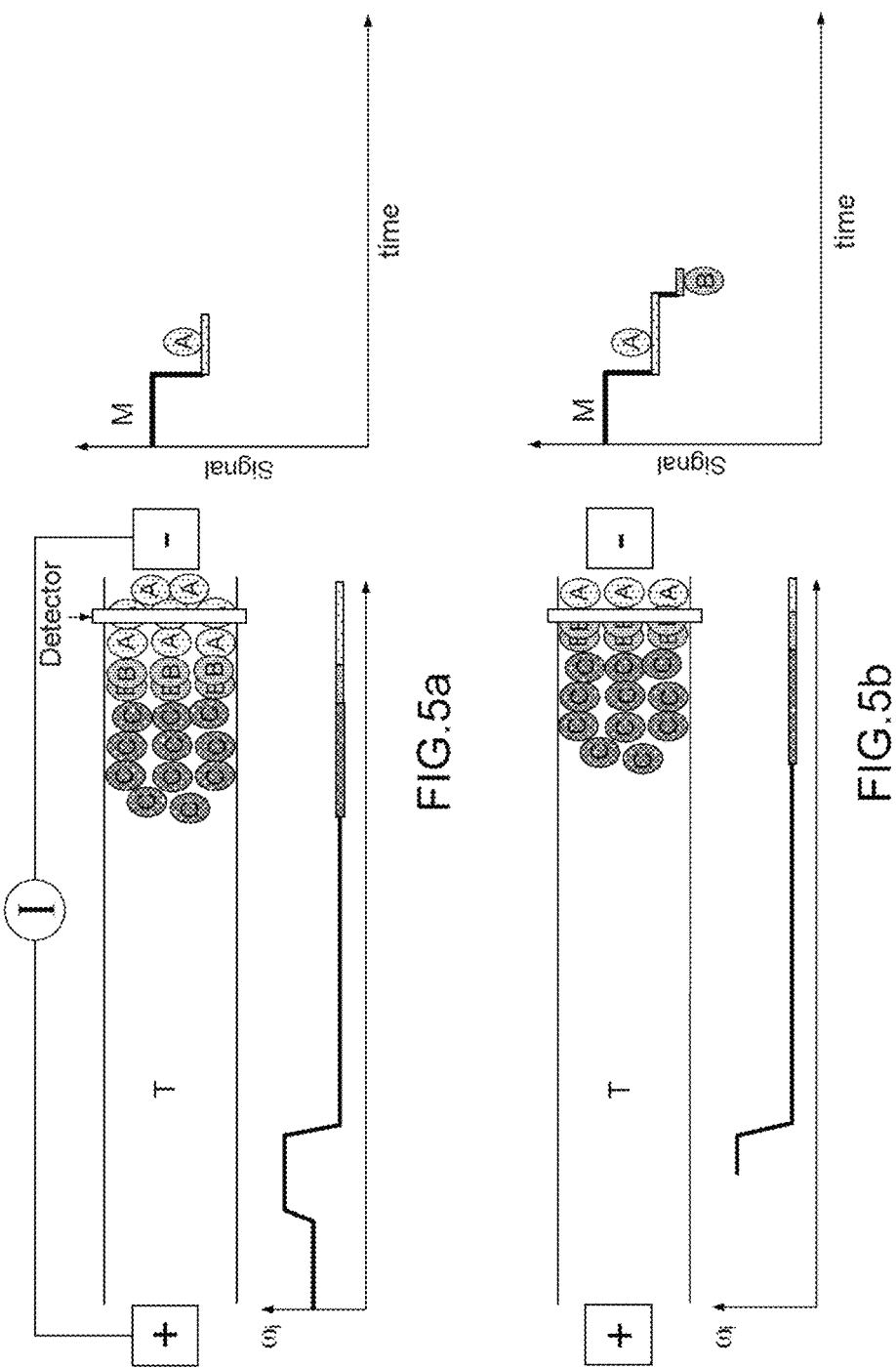

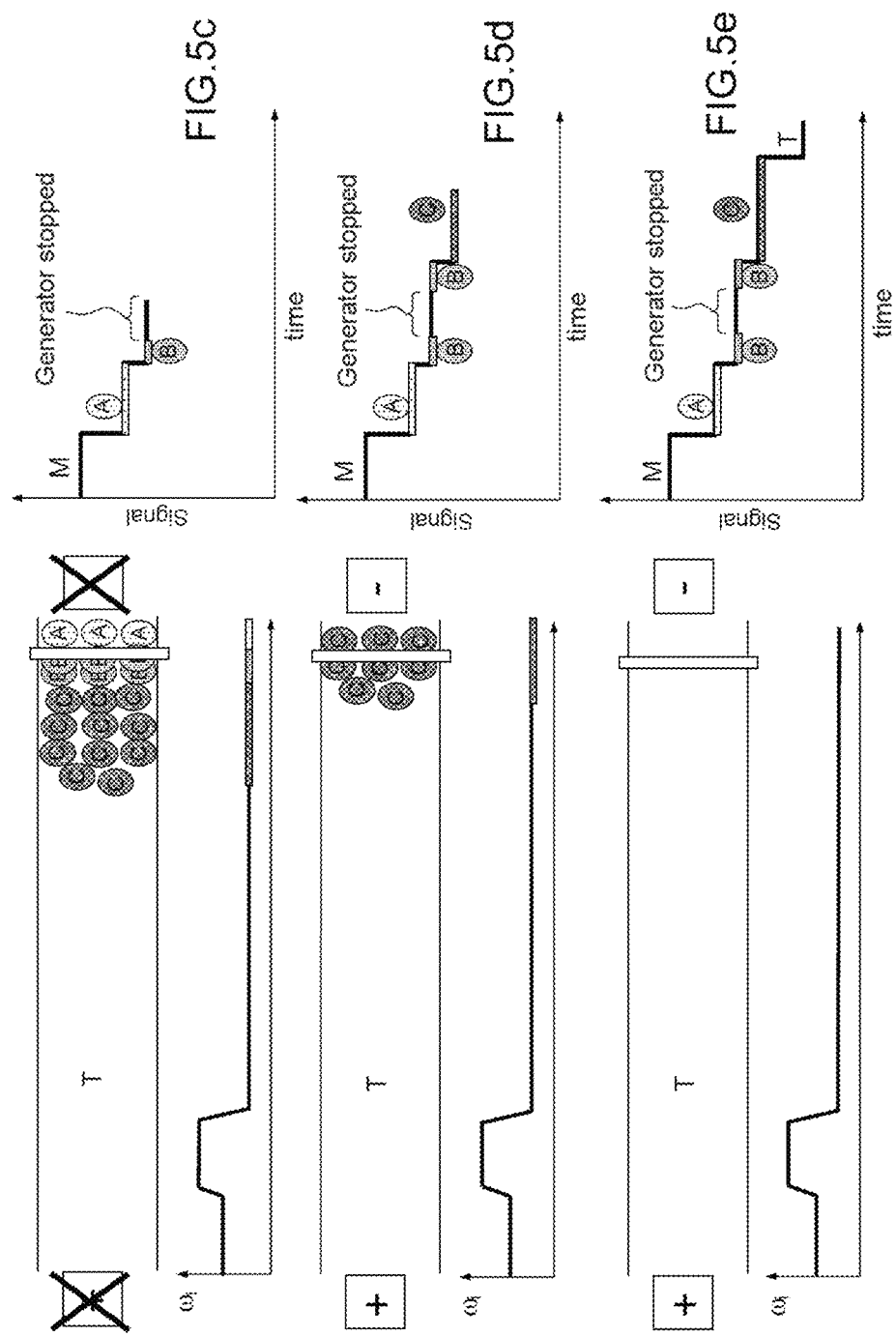

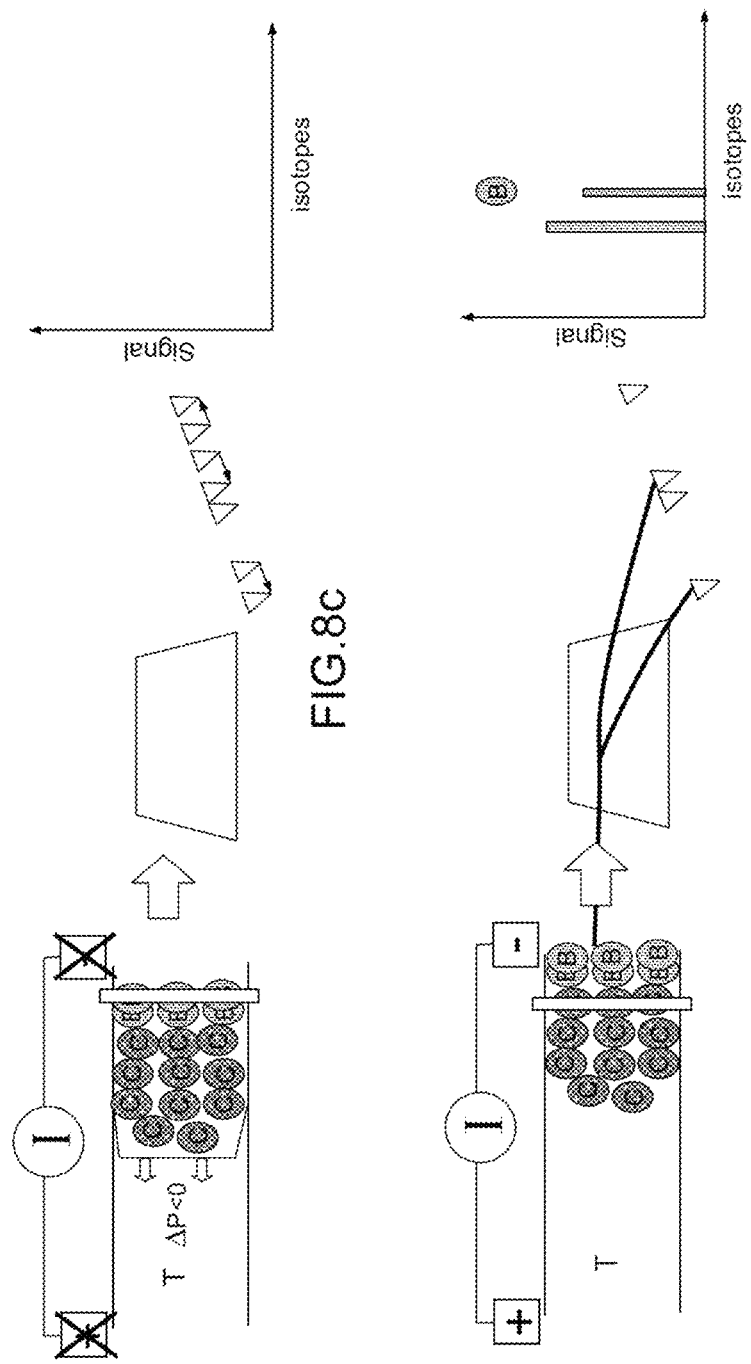

MULTI-ELEMENT ISOTOPIC MEASUREMENT BY DIRECT COUPLING OF A MULTI-CYCLE ISOTACHOPHORESIS TECHNIQUE AND A MASS SPECTROMETRY TECHNIQUE

CROSS-REFERENCE TO RELATED APPLICATION

This application claims priority to foreign French patent application No. FR 1463134, filed on Dec. 22, 2014, the disclosure of which is incorporated by reference in its entirety.

FIELD OF THE INVENTION

The present invention relates to the field of methods for qualitative or quantitative analysis of the constituents of a sample using a mass spectrometer equipped with an inductively coupled plasma source, more generally known as ICP-MS, for Inductively Coupled Plasma Mass Spectrometry.

The invention relates more particularly to a method for multi-element isotopic measurement of electrically charged species, and in particular of mineral or organometallic species contained in a solution, using a spectrometer of the ICP-MS type.

BACKGROUND

Isotopic measurement is notably performed in the nuclear area, and environment, geosciences and life sciences.

Isotopic measurement consists of determining the presence and/or concentration of one or more isotopes of a chemical element in a sample.

Each element of the periodic table has one or more isotopes, i.e. different atoms of one and the same element. Two isotopes of one and the same element have the same number of protons and electrons but a different number of neutrons.

Typically, iron, denoted Fe, has stable isotopes of masses 54, 56, 57 or 58 atomic mass units (amu) denoted $^{54}$Fe, $^{56}$Fe, $^{57}$Fe and $^{58}$Fe.

Determination of the isotopic ratios consists of measuring the abundance of each of these isotopes and calculating their respective proportions.

In the case of iron, the isotopic ratio $^{56}$Fe/$^{57}$Fe equates to expressing the abundance of $^{56}$Fe relative to that of $^{57}$Fe.

Isotopic measurements notably make it possible to determine:

the isotopic abundances of the different isotopes of one and the same element, the precise concentration of a particular element in solution by adding a known proportion of a tracer, the latter being perfectly characterized in terms of isotopic composition and concentration. This method is known as simple isotopic dilution, the abundance ratio between two isotopes of different elements (e.g. $^{145}$Nd/$^{238}$U) by adding a double isotopic tracer (e.g. $^{148}$Nd/$^{233}$U) by the method called double isotopic dilution.

The method of simple isotopic dilution consists of adding a tracer that is the same element but of different isotopic composition, for example enriched in one of the isotopes of the element to be determined, to the sample. This method makes it possible to effect elemental measurements of great precision, without a calibration straight line, as the isotopic composition and the concentration of the tracer are known perfectly, and based on measurement of the isotopic ratios.

Isotopic measurements require the use of instruments, such as mass spectrometers, capable of supplying a selective response to one or more given atomic masses, the intensity of the response having to be proportional to the abundance of the isotopes.

The technique most commonly used is ICP-MS. Spectrometers of the ICP-MS type consist of a plasma torch and a mass spectrometer. The plasma torch generally contains a rare gas (argon in most cases) which, under the action of an electric discharge and a radiofrequency field, generates a plasma that ionizes, with an efficiency close to 1, most of the elements introduced into the torch in elemental form or as compounds. Spectrometry of the ICP-MS type has been an indispensable analytical technique for many years. It allows rapid analysis of the majority of the elements of the periodic table qualitatively and quantitatively, while having good reproducibility, sensitivity, resolution, and a linear relation between the amount of the species to be analysed and the signal detected.

To obtain the best possible precision for measuring isotopic ratios, it is necessary to use a multicollector ICP-MS (MC-ICPMS), which allows the abundance of several isotopes to be measured simultaneously. This type of equipment notably is free from the instability of the ion beam at the level of the source of the mass spectrometer.

However, when the solution to be analysed comprises several charged species of very similar atomic mass (isobaric), prior to measurement it is necessary to separate the species individually with a chemical separative technique such as liquid chromatography or capillary electrophoresis.

In fact, despite the high resolving power of spectrometers of the ICP-MS type, they are not capable of resolving or differentiating all the isobaric interferences.

Isobaric interference is the term used when two isotopes of different elements have atomic masses whose difference is between 0.001 and 0.9 atomic mass unit.

For example, separation of two isotopes of two different elements such as neodymium of exact mass 149.9209 ($^{150}$Nd) atomic mass units (amu) and samarium ($^{150}$Sm) of exact mass 149.9173 amu requires a resolving power above 40000, well above the capabilities of spectrometers of the ICP-MS type.

Resolving power means the ability of a mass spectrometer to separate an ion of mass M from an ion of mass M+ΔM, with R=M/(M+ΔM).

In practice, a chemical separative technique and a spectrometer of the ICP-MS type may be combined by indirect coupling or "off-line", or by direct coupling or "on-line".

In indirect coupling, isotopic measurement is performed twice.

Firstly, the species contained in the solution are separated and then collected individually at the end of the separative technique. Secondly, each fraction collected is dried by heating, put back in solution with dilute nitric acid and then analysed with the spectrometer of the ICP-MS type. Each fraction then contains a single species (a single element) and there is no longer isobaric interference. The signal measured by the spectrometer of the ICP-MS type is stationary or constant as the solution containing the element previously separated is introduced continuously, which has the advantage of ensuring stability during the measurements of isotopic ratios, and consequently improving the measurement precision.

However, indirect coupling has the drawback of requiring steps of collection and treatment of previously separated fractions. These steps are difficult to automate and significantly increase the duration of the whole analysis process.

In direct coupling, isotopic measurement is performed in a single sequence. Once separated, the species are introduced directly, or in other words, introduced into the spectrometer of the ICP-MS type without a time gap between each species. Coupling of the chemical separation technique with the spectrometer is effected via a suitable interface. Direct coupling therefore dispenses with treatment of the collected fractions that is inherent in indirect coupling, notably making it possible to reduce the analysis time.

Thus, the document "Pitois A. et al., International Journal of Mass Spectrometry, 2008, 270, pages 118-126" proposes isotopic measurement in which fission products of a solution of nuclear fuel are separated by electrophoresis using a capillary electrophoresis device connected by direct coupling to a spectrometer of the ICP-MS type.

FIG. 1 shows a flow sheet of isotopic measurement by direct coupling via a coupling interface 10 between a device for separating the species and a mass spectrometer of the ICP-MS type, the coupling interface 10 comprising a nebulizer 9 in the figure and a sorting chamber 12. On leaving the separating device 20, the species to be analysed A, B, C are introduced into the nebulizer 9, in which the species A, B, C are transformed into aerosol comprising fine droplets and a carrier gas (generally argon). The number of species to be analysed can of course be greater than three.

The finest droplets comprising the species A, B, C are then selected in a sorting chamber 12 so as to convey a stable, homogeneous aerosol to the plasma torch 13 of the ICP-MS spectrometer. On leaving the plasma torch 13, the species A, B, C are desolvated, atomized and ionized. The ions are then extracted from the plasma by means of extraction cones 14 and then focused by focusing lenses 15, before entering the ICP-MS spectrometer. Under the action of a magnetic field generated by a magnet 16, the ion beams corresponding to the different isotopes are separated following individual circular paths that depend on the mass/charge ratio of the isotopes to be analysed. Information on the abundance of the isotopes is obtained by placing in their path detectors 17, which record, simultaneously and continuously, the intensity of each of the beams of mono-isotopic ions. MC-ICPMS spectrometers generally have from 9 to 16 detectors 17.

Another document of the prior art EP 2646813 discloses a method for isotopic measurement in which coupling between the separative technique and the ICPMS spectrometer notably allows measurement that can be automated and is of reduced duration, with improved reproducibility and resolution, in particular when the solution comprises several elements having one or more isobaric interferences.

The separative methods used conventionally, such as chromatography or electrophoresis, allow individual separation of the species A, B, C, which are eluted in the form of single-element peaks of triangular shape, as shown schematically in FIG. 2a.

This type of peak only allows a small number of measurement points in unit time.

Moreover, there are large variations of signal amplitude between two consecutive points, which cause instability and especially imprecision of measurement by the spectrometer of the ICP-MS type.

In the isotachophoresis configuration of an electrophoresis device, once separation has been performed, elution takes place in the form of bands, as shown in FIG. 2b, thus allowing more precise measurements to be obtained.

Isotachophoresis (ITP) is a method for separating species as a function of their electric charge/size ratio. The device used for carrying out this method is a conventional capillary electrophoresis device.

The capillary electrophoresis device consists essentially of two reservoirs connected by a capillary column, each reservoir containing an electrolyte and an electrode. After a voltage is applied between the two electrodes, the species introduced into the capillary filled with electrolyte separate according to their speed of electrophoretic migration, which is a function of their electric charge/size ratio. The separated species are then detected using a suitable analytical technique.

The isotachophoresis mode of capillary electrophoresis is characterized by the use of a discontinuous separation medium comprising a leading electrolyte M and a terminating electrolyte T of different composition, between which the solution S to be analysed is inserted contiguously. The leading electrolyte M has the highest speed of electrophoretic migration of the device, and the terminating electrolyte T has the lowest speed of electrophoretic migration of the device. The leading electrolyte M and terminating electrolyte T are positioned after the inlet and before the outlet of the capillary, respectively.

The composition of the electrolytes must therefore take account of the value of the speeds of electrophoretic migration of the species, otherwise these species will not be separated.

After a voltage is applied between the ends of the capillary (capillary inlet and outlet), the species, under the effect of a current of constant intensity or of a constant electric field, will gradually become arranged according to their speed of electrophoretic migration until a state of equilibrium is reached called quasi-stationary. The species are then distributed in their individual, clearly delimited contiguous elution bands. The species are therefore concentrated or diluted as a function of their initial concentration in the solution.

Isotachophoresis therefore differs from the conventional implementation of capillary electrophoresis by the use of a discontinuous separation medium, comprising at least two electrolytes instead of just one, but also by the fact that, since the concentration of a species is homogeneous at all points of the elution zone obtained in isotachophoresis, its detection is reflected in a signal of constant or approximately constant amplitude within this zone, rather than a peak reflecting a variation of concentration over time. The number of measurement points that can be recorded by the ICP-MS spectrometer depends on the width of the elution zone.

The principle of separation by isotachophoresis may be summarized as shown in FIGS. 3a-3c.

A leading electrolyte M, a solution S comprising the species A, B and C, and a terminating electrolyte T are injected in that order into a capillary 30, with the terminals of the capillary 30 connected to a voltage generator designated I (FIG. 3a).

The leading electrolyte M determines the speed of electrophoretic migration, and it is selected so as to have the highest speed of electrophoretic migration of the system.

In contrast, the terminating electrolyte T has the lowest speed of electrophoretic migration of the system.

The composition of the electrolytes must therefore take account of the species of interest, otherwise these species will not be separated. The leading M and/or terminating T electrolytes generally have a concentration between 1 mM and 100 mM, preferably between 10 mM and 20 mM. They generally possess buffering power.

The terminating electrolyte T may be a zwitterionic compound such as carnitine chloride or a carboxylic acid such as acetic acid. Preferably, the leading electrolyte M and terminating electrolyte T are aqueous solutions comprising elements such as oxygen, hydrogen, nitrogen and carbon so as to allow easy destruction at the end of analysis.

Under the effect of the current of constant intensity (or constant electric field) from some tens of nanoamperes to some tens of microamperes (or from some volts to kilovolts, respectively), the species A, B and C are reorganized as a function of their speed of electrophoretic migration, creating a gradient of speed between the terminating electrolyte T and the leading electrolyte M (FIG. 3b).

At the end of this reorganization (FIG. 3c), the species A, B and C are separated and concentrated in contiguous single-element bands between the leading electrolyte M and the terminating electrolyte T. The species A, B and C as well as the leading M and terminating T electrolytes then migrate at an identical speed imposed by the leading electrolyte M.

The performance of an isotachophoresis separation system is defined by the concept of resolution or degree of purification of the species.

Ohm's law (Equation 1), which applies during separation, relates the conductivity a of a sample to the length L and to the inside diameter d of the capillary 30 as well as to the value of voltage U of the voltage generator.

$$U = \frac{4I}{\pi\sigma} \cdot \frac{L}{d^2} \quad \text{(Equation 1)}$$

When a solution S comprising a high concentration of one of the elements relative to the trace elements is injected, it is necessary to increase the amount of solution S to be injected into the capillary 30 so as to obtain bands comprising the trace elements of significant length, which improves the separation capacity.

This optimization of the separation capacity involves reducing the inside diameter d of the capillary 30 or increasing the length of the capillary L.

For example, if the size of the capillary is 3 m and the voltage is 30 kV, a voltage of 1 kV is obtained for each 10 cm fraction. If the length of the capillary is increased to 30 m, the voltage at the terminals of a fraction of length 10 cm drops to 0.1 kV.

To maintain a voltage of 30 kV at the terminals of the capillary 30, it would be necessary to keep the length L of the capillary 30 and increase the inside diameter d, which would degrade the separation capacity of the system.

A work by F. M. Everaert et al. "*Isotachophoresis, experiments with electrolyte counterflow*", J. Chromatogr. 60(1971) 397-405, proposes applying a continuous counter-pressure in the direction opposite to the direction of electrophoretic migration of the species A, B and C so as to slow down the speed of migration of the species.

Another work by S. Bhattacharyya et al. "Sample dispersion in isotachophoresis with Poiseuille counterflow", Phys. Fluids 25 (2013) also investigates this possibility. This study concludes that the application of a continuous counter-pressure during separation of the species by isotachophoresis is accompanied by an increase in dispersion, which reduces the efficiency of purification of the species, and particularly of the trace elements.

SUMMARY OF THE INVENTION

Thus, one aim of the invention is to propose a method of separation for separating the elements having isobaric interferences, notably without diminishing the efficiency of purification.

A method is proposed for separating electrically charged species in a solution by an isotachophoresis method comprising:

a first step in which a leading electrolyte having the highest speed of electrophoretic migration, a solution comprising charged species having their own individual intermediate speeds of migration and a terminating electrolyte having the lowest speed of migration are introduced into the inlet of an electrophoresis capillary, in that order.

The following steps are repeated until separation of at least one charged species contained in the solution is obtained:

a second step in which a voltage is applied between the two ends of the capillary so as to start separation of the species, a third step in which the voltage is stopped, a fourth step in which a counter-pressure is applied so as to displace the species towards the inlet of the capillary, the speed of displacement of the species during application of the counter-pressure being lower than the speed of electrophoretic migration of the species under the effect of the electric current.

Advantageously, the species are displaced to the level of the inlet of the capillary.

Stopping the voltage and transient application of a counter-pressure makes it possible to utilize the length of the capillary several times and extend the separation distance artificially.

According to one embodiment, the method further comprises a fifth step in which isotopic ratio measurement is performed by mass spectrometry coupled to an inductive plasma source (ICP-MS) for all the electrically charged species contained in the solution and separated by isotachophoresis, the mass spectrometer being directly coupled to the electrophoresis device.

According to another embodiment, in a fifth step, a first species separated prior to the third step of stopping the electric field is recovered after the second step of application of the voltage, making it possible to keep only the species present at trace levels, notably. This embodiment makes it possible to extract a species with a higher speed of migration than the other species of the system and thus improve the performance of separation of the remaining species while separation is continued.

Advantageously, the method further comprises a sixth step in which isotopic ratio measurement is performed by inductively coupled plasma mass spectrometry of the first species separated by isotachophoresis before continuing isotachophoresis separation of the other electrically charged species of the solution, the mass spectrometer being directly coupled to the electrophoresis device.

Direct coupling avoids the collection steps, which decreases the amounts of solvent to be reprocessed at the end of analysis.

Advantageously, the capillary electrophoresis device is at least partly a microfluidic system.

Advantageously, the inductively coupled plasma mass spectrometer (ICP-MS) is of the multi-collection type (MC-ICPMS), allowing detection of several isotopes simultaneously.

Advantageously, the method further comprises a seventh step allowing ad hoc repositioning of the detectors of the mass spectrometer on stopping the voltage, allowing multi-element isotopic analyses to be carried out on a solution comprising a larger number of isotopes than there are detectors present on the MC-ICPMS.

The method proposed is particularly advantageous for separating electrically charged species comprising mineral anions, mineral cations, organometallic compounds, transition metals, alkali metals, alkaline-earth metals, lanthanides and/or actinides or mixtures thereof and where at least two electrically charged species display isobaric interference such that the atomic mass difference between the charged species is between 0.001 and 0.9 atomic mass unit (amu).

Advantageously, the leading and/or terminal electrolyte is an aqueous solution of a compound comprising the elements carbon and oxygen.

BRIEF DESCRIPTION OF THE DRAWINGS

The invention will be better understood and other advantages will become clear on reading the following description, given as a non-limiting example, and from the appended figures, where:

FIGS. 5a, 5b, 5c, 5d and 5e show the progress of an isotachophoresis analysis having stopping of separation, according to one aspect of the invention, FIGS. 8a, 8b, 8c, 8d show the progress of multi-element measurement of isotopic ratios by direct coupling of a method of sequential multi-cycle isotachophoresis and a method of spectrometry using a multicollector inductively coupled plasma mass spectrometer.

DETAILED DESCRIPTION

The Kohlrausch regulation function (KRF) is a law of conservation that describes the mechanism of electrophoretic migration of ions when they are subjected to a current of constant intensity, this law being expressed by relation (2):

$$\sum_{i=1}^{n} \frac{|Z_i|C_i}{\mu_i} = Wx \qquad \text{Equation 2}$$

$Z_i$ is the valence of the ions
$C_i$ is the concentration
$\mu_i$ is the mobility and
$Wx$ is a constant defined for each point of the electrophoretic system.

This law defines a constant $Wx$ for each zone of electrolyte. In other words, the leading electrolyte M has a constant $Wx(M)$, the solution S has a constant $Wx(S)$ and the terminating electrolyte T has a constant $Wx(T)$. These values of constants remain unchanged during migration of the species. In other words, when a species migrates from a point x1 having a constant KRF1 to a point x2 having a constant KRF2, the concentration of the species under consideration evolves so as to respect the new constant KRF2. Thus, if KRF1 is greater than KRF2, the species under consideration is diluted, extending the distance over which it can be detected.

Figure 4A:
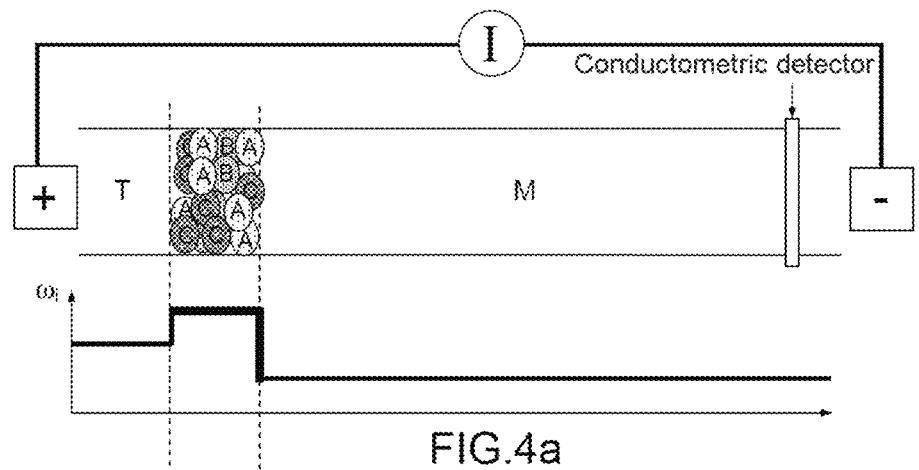
FIGS. 4a, 4b, and 4c show the progress of an isotachophoresis analysis, according to the known prior art.
Figure 4B:
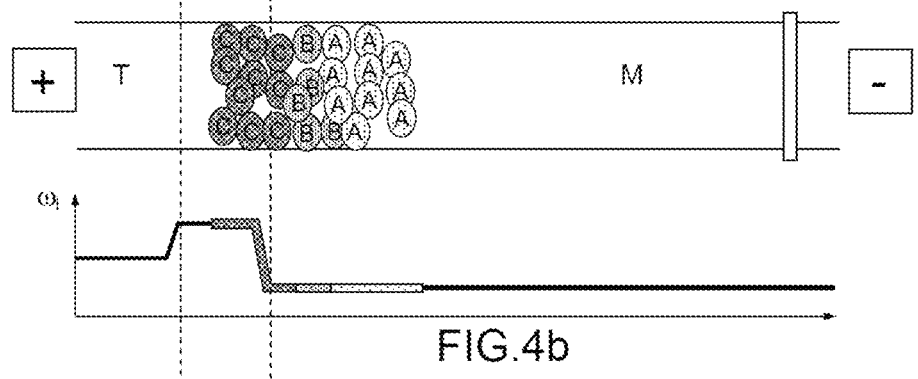
Figure 4C:
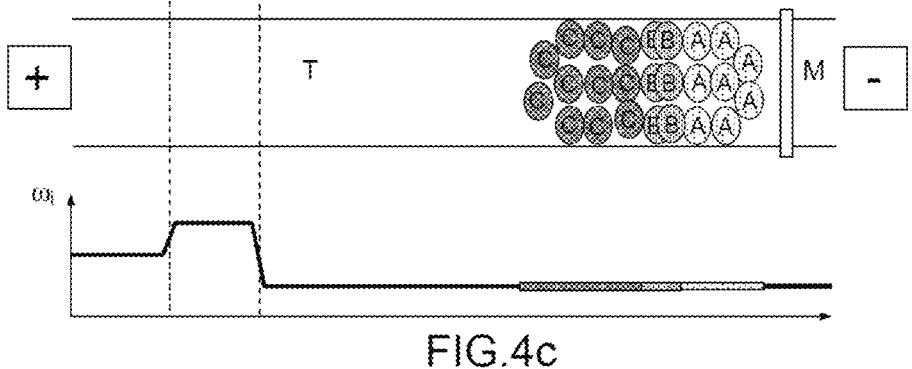

FIGS. 4a-c show the progress of a conventional isotachophoresis analysis. These figures notably demonstrate the effect of the Kohlrausch function described above on the electrophoretic migration of the species.

Figure 1:
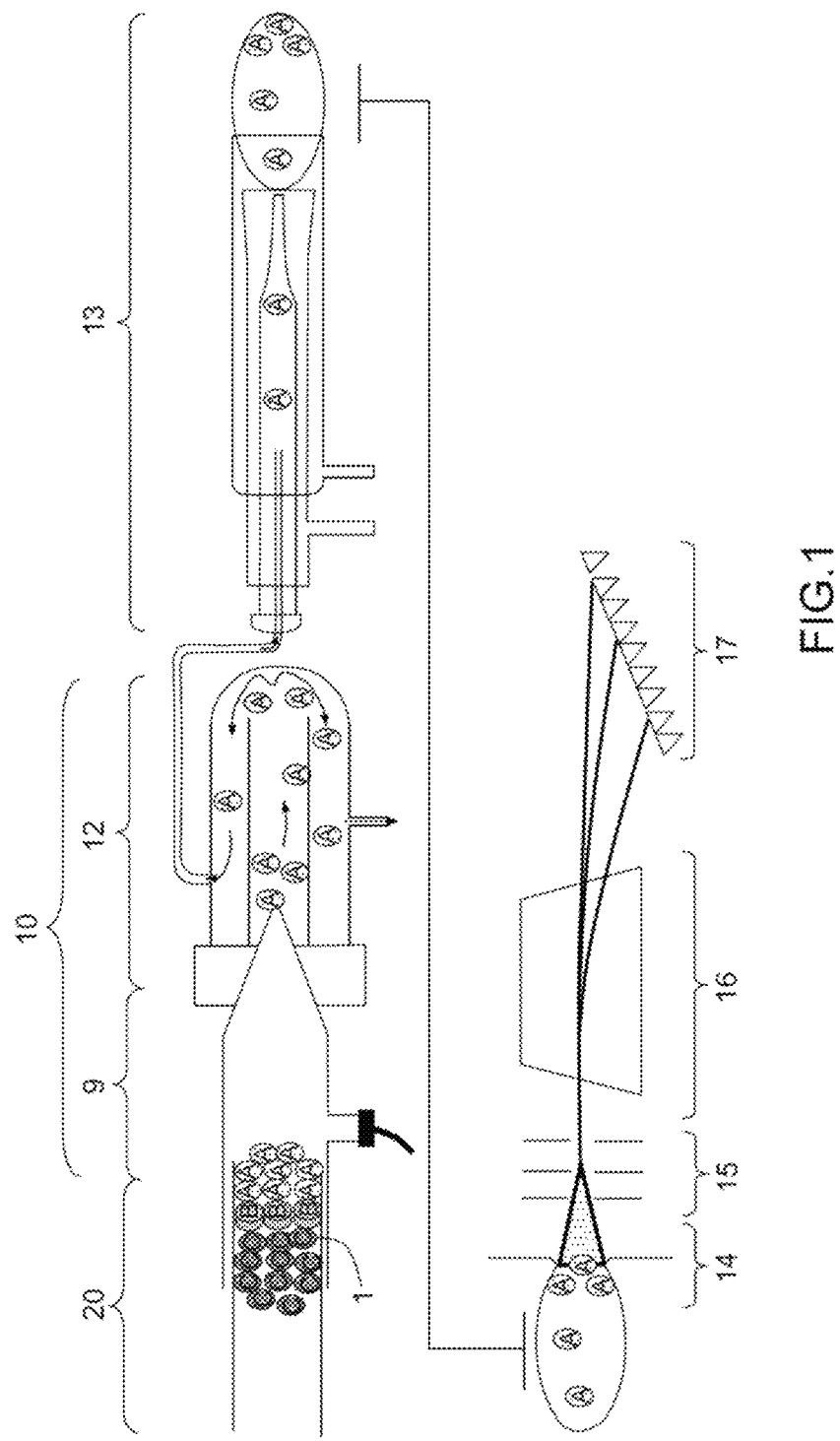
FIG. 1, already described, shows a schematic diagram of a device for carrying out isotopic measurements by "on-line" coupling of a chemical separation technique with a multicollector inductively coupled plasma mass spectrometer (MC-ICPMS), FIGS. 2a and 2b, already described, show the elution profiles obtained by a conventional chemical method of separation and by isotachophoresis, respectively, FIGS. 3a, 3b and 3c, already described, show a flow sheet of the process for separating three species by isotachophoresis, according to the known prior art.
Figure 2A:
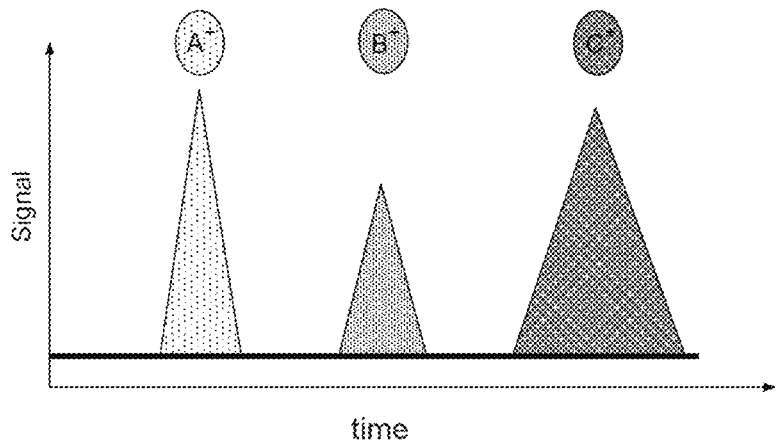
Figure 2B:
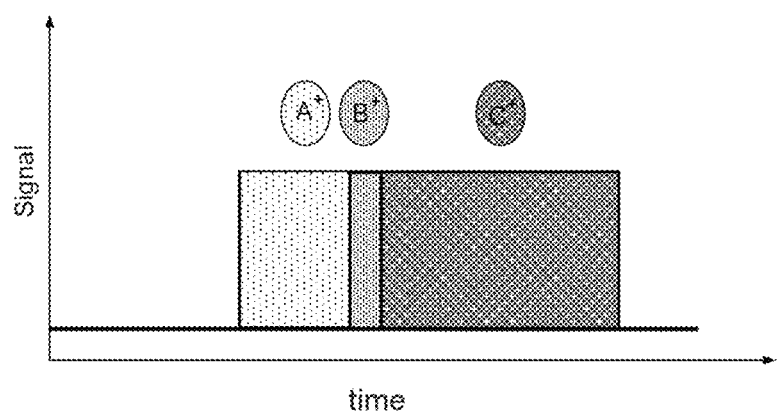
Figure 3A:
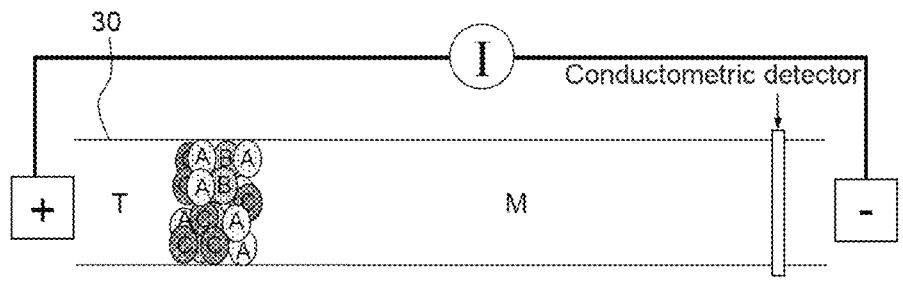

FIG. 4a shows a capillary in the initial state as described in FIG. 3a. In the present case, the leading electrolyte M has a constant $Wx(M)$, the solution S has a constant $Wx(S)$ and the terminating electrolyte T has a constant $Wx(T)$.

The values of the KRF constants are shown in a diagram as a function of the coordinate x where we are located in the capillary 30.

FIG. 4b shows the capillary 30 in which the species A, B, and C are undergoing migration.

For example, when the species C migrates towards the leading electrolyte M and the value of the KRF constant of the solution $Wx(S)$ is greater than the value of the KRF constant $Wx(M)$ of the leading electrolyte M, dilution of the species C takes place, so that the value of the concentration respects the value of the KRF constant $Wx(M)$ of the leading electrolyte M. In other words, the concentration of species C decreases through increase in the distance over which species C is detected.

In FIG. 4c, separation of the species A, B and C is completed. The species A, B, C are distributed in the form of contiguous single-element bands.

Moreover, in FIG. 4c, the terminating electrolyte T illustrates the Kohlrausch law of conservation. The terminating electrolyte T is concentrated at the inlet of the zone corresponding initially to the zone of the solution S, whereas the terminating electrolyte T is then diluted at the inlet of the zone corresponding initially to the zone of the leading electrolyte M. Thus, the concentration of the terminating electrolyte is not constant along the capillary 30, which is reflected in the graph showing the values of constant KRF as a function of x.

Isotachophoresis is a technique that differs from the other techniques for chemical separation by its capacity for autofocusing of the species in separate bands, whose length varies during separation and then remains constant once the quasi-stationary state is reached. It is this characteristic that is peculiar to the isotachophoresis technique that is exploited by the invention.

Quasi-stationary state means the state of the system once separation has been effected.

This particular property makes it possible to stop and resume separation with limited degradation of the performance of the technique. Thus, a principle of one aspect of the invention is based on a step of transient stoppage of the generator of voltage at the terminals of the capillary 30, which has the result of stopping the migration of the species to be separated.

FIGS. 5a-e show the progress of an isotachophoresis analysis during which the voltage generator is stopped temporarily.

FIG. 5a shows a capillary 30 in which the species A, B, C have been separated by isotachophoresis, as shown in FIG. 4c. The representation of the conductometric signal, obtained by a detector situated at the outlet end of the capillary as a function of time, has a first plateau corresponding to the leading electrolyte M and a second plateau corresponding to species A.

FIG. 5b shows the capillary 30 when detection of species B begins. A second plateau corresponding to species B appears on the graph of the conductometric signal as a function of time.

FIG. 5c shows the capillary when the voltage generator is stopped. The migration of the species is halted, species B remains opposite the detector, which is reflected by an increase in the length of the plateau corresponding to species B.

FIG. 5d shows the capillary 30 when migration resumes, migration of species B comes to an end, and species C is then detected. A new plateau corresponding to species C then appears on the associated graph of the conductometric signal as a function of time.

Finally, FIG. 5e shows the capillary 30 during passage of the terminating electrolyte T at the level of the detector. The signal, as a function of time, has a fourth plateau corresponding to the terminating electrolyte T.

The different steps of separation can be repeated if separation of species B and C has not been obtained.

These figures clearly demonstrate that transient stoppage of the voltage generator leading to stopping of migration of the species does not cause the system to change. In other words, temporary stoppage of migration does not have an influence on separation by isotachophoresis.

FIGS. 6a to 6e show the progress of an analysis by isotachophoresis during which the voltage generator is stopped after one cycle of migration and a counter-pressure is applied transiently.

Figure 3B:
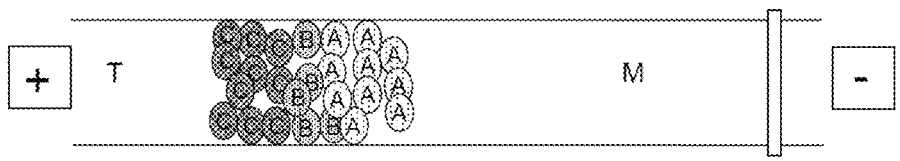
Figure 3C:
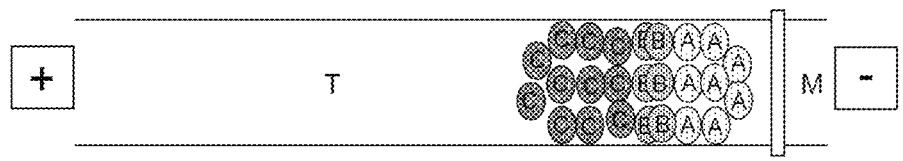
Figure 6A:
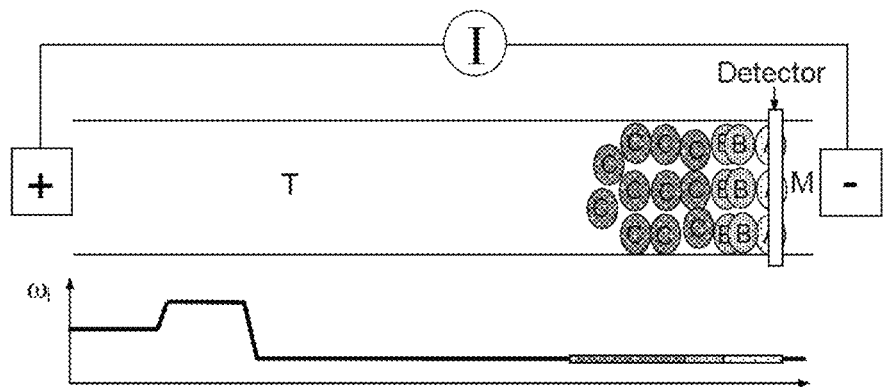
FIGS. 6a, 6b, 6c, 6d and 6e show the progress of an isotachophoresis analysis with multiple utilization of the separation length, according to another aspect of the invention.

FIG. 6a shows the capillary in which the species A, B, and C have migrated to the level of the detector near the outlet of the capillary 30, after a first cycle of separation. Separation of the species A, B and C has started, according to the principle described in FIGS. 3a-3c, but is not yet completed. In fact, one portion of species A has been isolated but the other portion of species A and species B and C are still mixed.

Figure 6B:
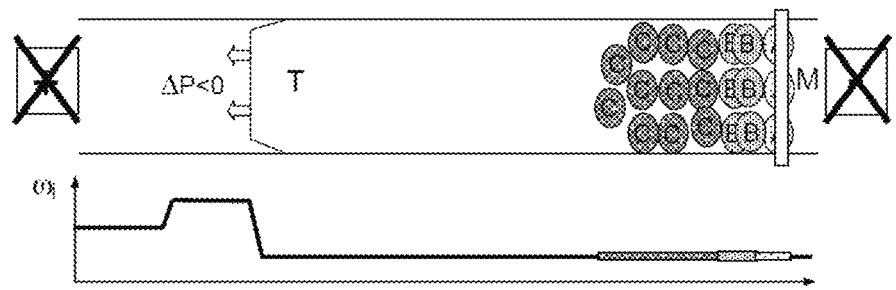

FIG. 6b corresponds to a step of stopping the electric field and applying a counter-pressure ΔP in the direction opposite to the direction of migration of the species so as to return all the species A, B, C to the level of the inlet of the capillary 30.

Application of the counter-pressure ΔP mixes species A, B and C again. Thus, it is necessary to configure the counter-pressure ΔP so that agglomeration or mixing of the species does not completely cancel the start of separation obtained by the first cycle of separation. More precisely, the speed of return of species A, B, C to the inlet of the capillary must be lower than the speed of migration of species A, B, C during the first cycle of separation.

Advantageously, a second detector is positioned at the level of the inlet of the capillary so as to stop the application of the counter-pressure when species A, B and C arrive at the level of the inlet of the capillary 30.

Figure 6C:
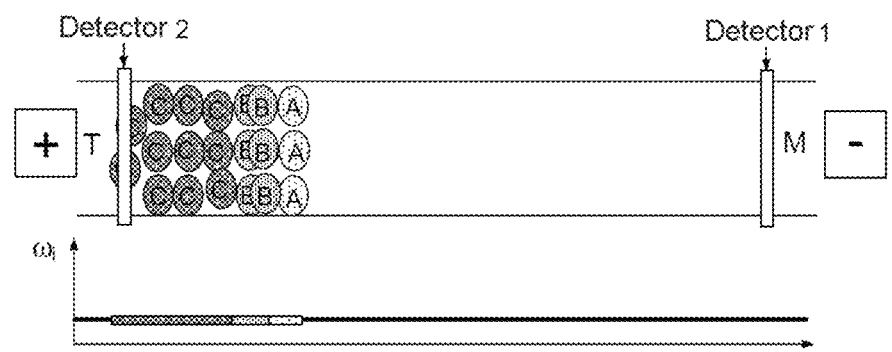

FIG. 6c shows the second cycle of migration of the species when migration resumes. Species A, B, and C resume their migration with a speed depending on their charge/size ratio, forming bands.

Figure 6D:
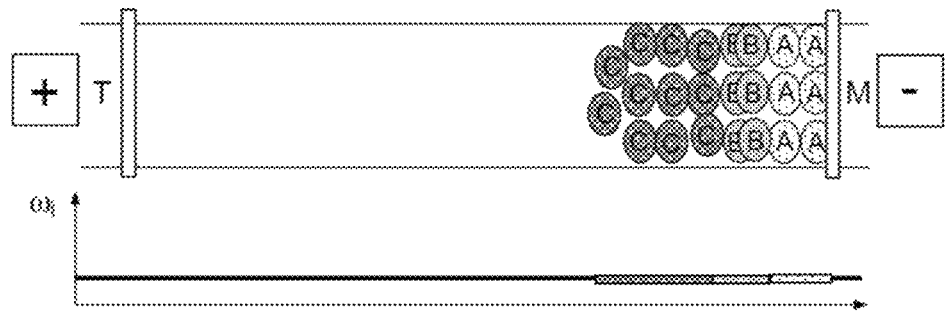

FIG. 6d corresponds to a stage of separation of the more advanced species; the single-element bands begin to appear.

Figure 6E:
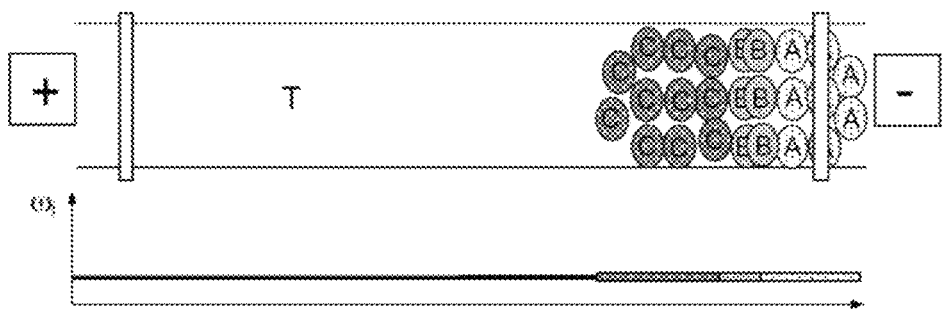

In FIG. 6e, separation is completed; species A, B and C are distributed in the form of single-element bands. The detector situated near the outlet of the capillary 30 then detects the different species, as in FIG. 5e.

FIGS. 7a to 7f show the evolution of the separation of a mixture of four lanthanides Nd, Sm, Eu and Gd introduced in identical amount, namely 177 ng, into a capillary with a length of 1 m and a diameter of 75 microns. Separation by isotachophoresis is effected by applying a current of 3 µA.

Figure 7A:
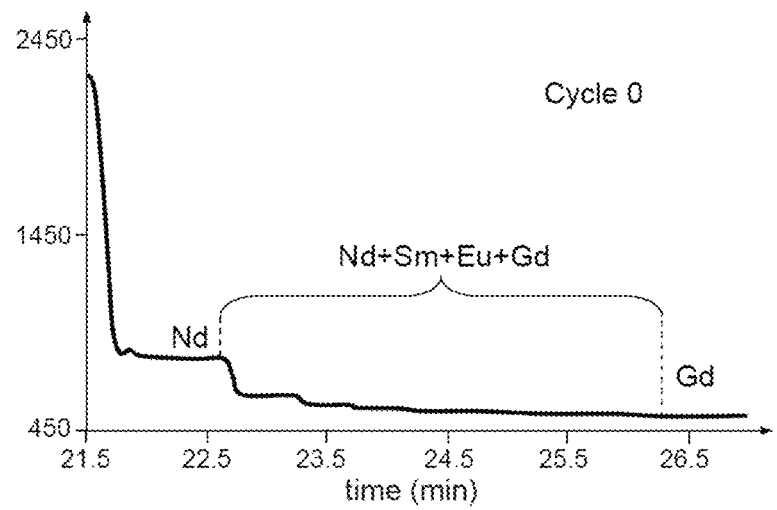
FIGS. 7a, 7b, 7c, 7d, 7e, 7f present graphs of intensity of the conductometric signals as a function of time, the graphs being obtained after each of the five measurement cycles using a conductometric detector.
Figure 7B:
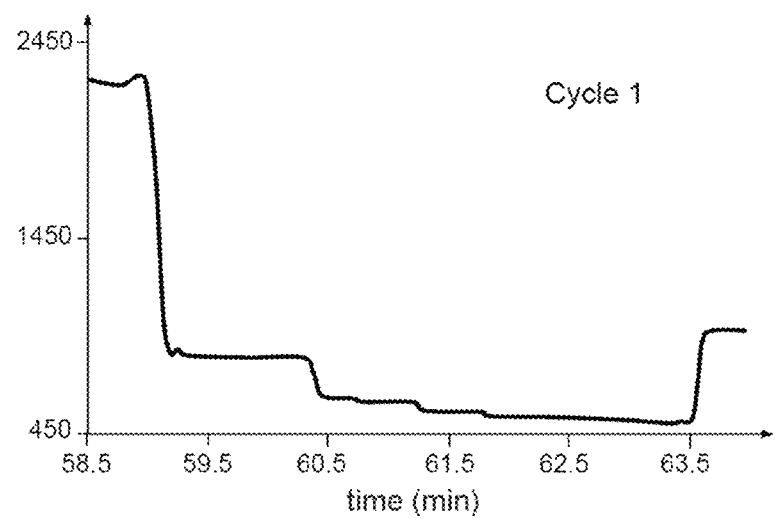
Figure 7C:
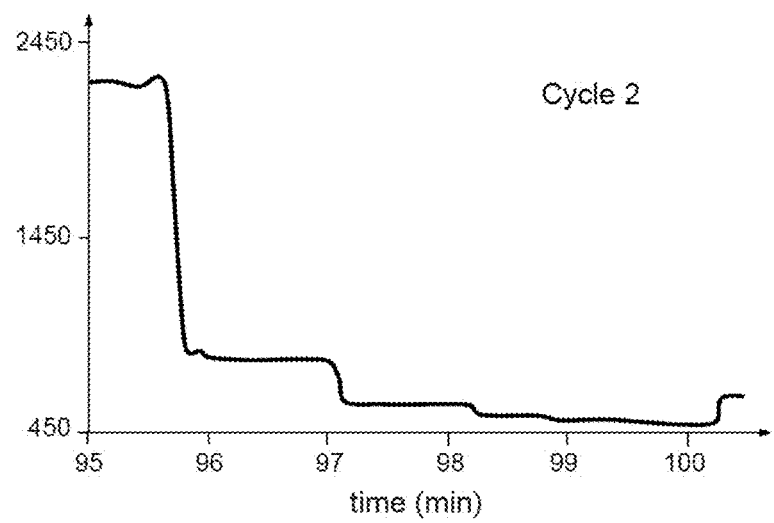
Figure 7D:
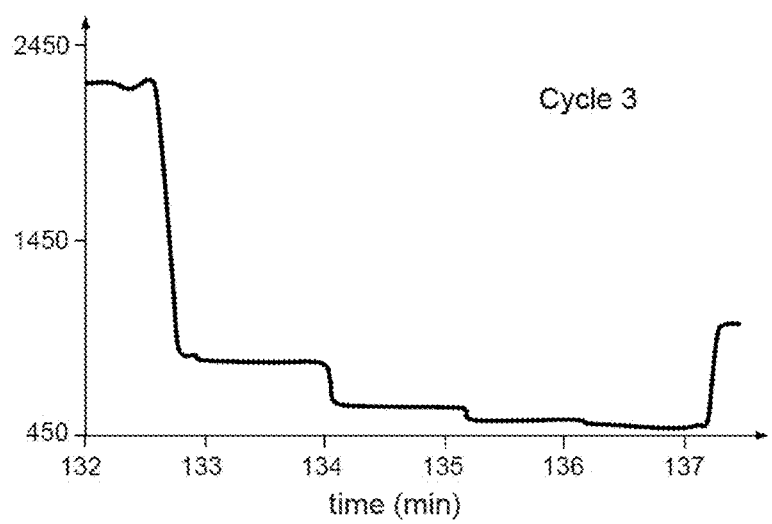
Figure 7E:
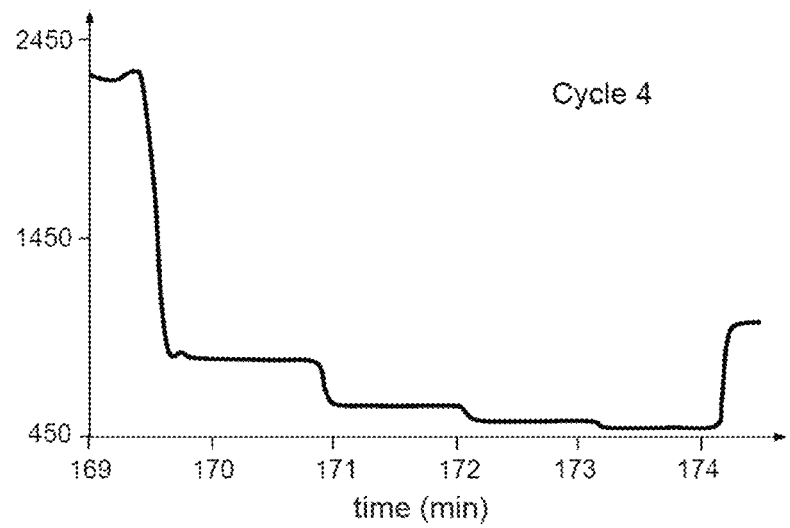
Figure 7F:
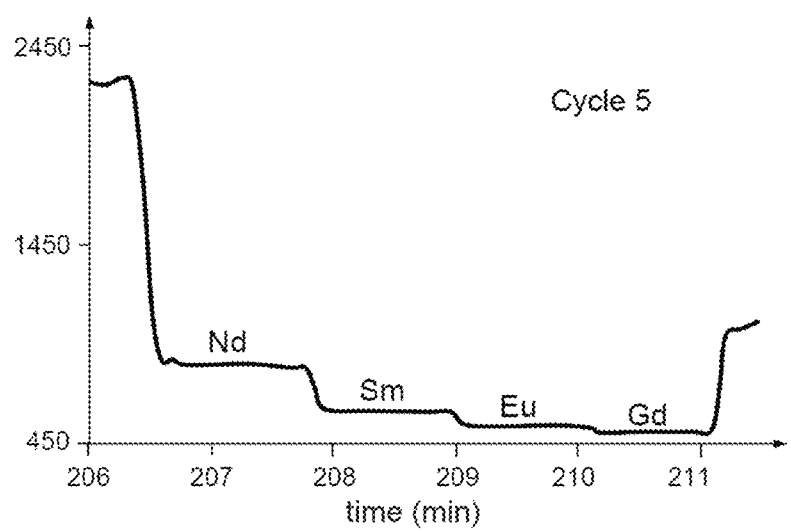

FIG. 7a shows that after one cycle of migration, it is not possible to separate these four lanthanides with a separation system used conventionally.

Effectively, after cycle 0, one portion of the neodymium has been isolated, and the other portion of the neodymium is still mixed with the samarium, europium and gadolinium. Thus, the graphical representation of the conductometric signal as a function of time has only two plateaux.

Separation of the four lanthanides is obtained after five repetitions of the various steps.

Multi-cycle isotachophoresis makes it possible to increase the length of the capillary artificially without needing to increase the voltage applied to the terminals of the capillary 30, thus making it possible to separate species that have similar speeds of electrophoretic migration.

The succession of cycles shown in FIGS. 7b to 7f shows a gradual evolution of the separation profile, leading to the formation of four bands corresponding to the four lanthanides.

Optionally, if one species has a speed of migration well above that of the other species, it is possible to extract it before continuing separation with the other species.

FIGS. 8a to 8d show the steps of the method of multi-element isotopic measurement coupling a method of multi-cycle isotachophoresis as described above and a method of mass spectrometry using a mass spectrometer of the multi-detector ICP-MS type.

Figure 8A:
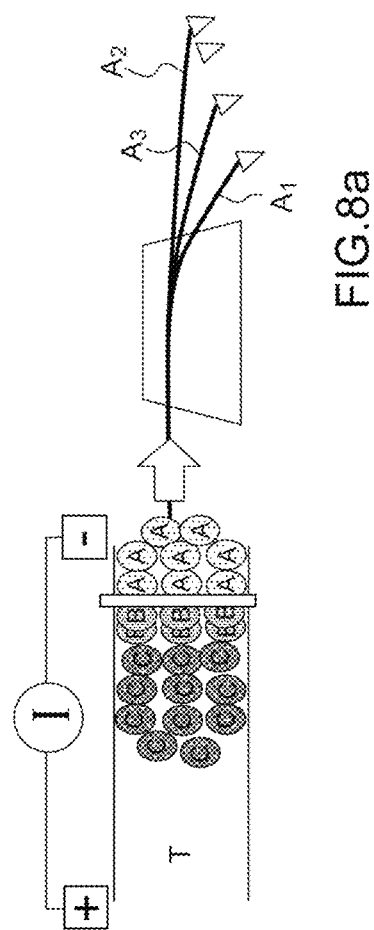

FIG. 8a shows a capillary after separation of species A, B and C, species A, B, and C being situated at the level of the outlet of the detector in the form of single-element bands, as shown in FIG. 6e.

Species A is transferred to the MC-ICPMS mass spectrometer. In the present case, three isotopes A1, A2, and A3 of element A are detected at the detectors. The graph showing the level of the signals by MC-ICPMS has three peaks corresponding to the three isotopes.

Figure 8B:
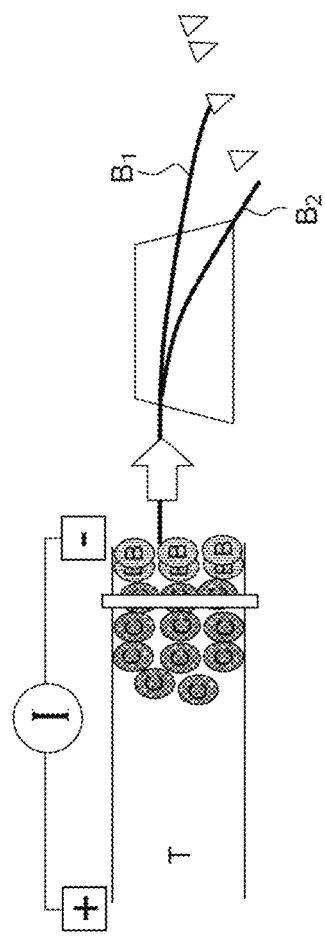

FIG. 8b shows the start of analysis of element B by MC-ICPMS; two isotopes B1 and B2 of element B are demonstrated. However, only one of the two isotopes B1 is detected at the level of the detectors of the MC-ICPMS spectrometer, the detectors not being positioned so as to detect the other isotope.

FIG. 8c corresponds to the step of stopping separation and applying counter-pressure so as to return the remaining species B and C to the inlet of the capillary. During this stoppage, the detectors of the MC-ICPMS spectrometer are repositioned so as to be able to detect the second isotope B2 of element B.

FIG. 8d corresponds to the step of isotopic measurement of species B after a new cycle of migration of the species. Species B is transferred to the MC-ICPMS spectrometer; the two isotopes B1 and B2 of species B are detected, which corresponds to the two peaks on the graph showing signal intensity as a function of time.

Figure 9:
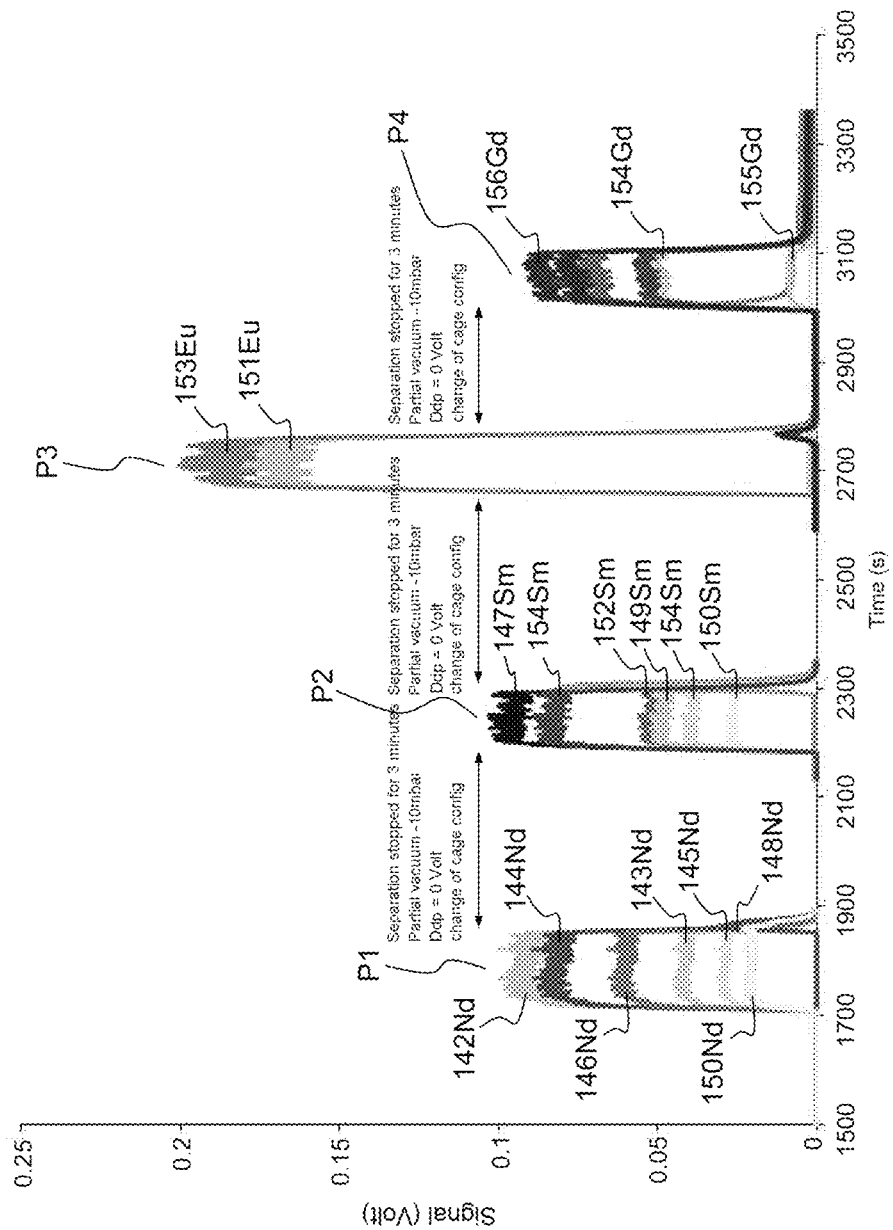
FIG. 9 is a graphical representation of the signals obtained by coupling with an ICPMS following analysis, according to the invention, of a mixture of four lanthanides having 29 isotopes.

FIG. 9 shows separation of a mixture of four natural lanthanide elements Nd, Sm, Eu and Gd having 29 isotopes.

This figure is able to confirm the validity of the method for multi-element isotopic measurement with delayed sequential elution. In fact, acquisition of the conductometric signals of the 29 isotopes was performed in a single separation.

Therefore 29 rectangular signals are obtained with similar widths, distributed in four groups each corresponding to one lanthanide element of the mixture. The graph shows measurement of the signals of the isotopes obtained by an MC-ICPMS spectrometer after separation by isotachophoresis according to the principle of the invention. In the present case the detectors are repositioned during the stoppages of separation so as to detect all the isotopes.

The graph of the signal as a function of time reveals four groups of curves P1, P2, P3 and P4. Separation of the mixture of lanthanides is stopped after appearance of each of the groups and a counter-pressure is applied. During application of the counter-pressure, the detectors are repositioned.

The first group of curves has a peak P1 at 1800s corresponding to the element neodymium, the second group of curves corresponding to the element samarium has a peak P2 at 2200 s, the third group of curves corresponding to the element europium has a peak P3 at 2700 s and the fourth group of curves corresponding to the element gadolinium has a peak P4 at 3000 s.

The first group comprises the plateaux corresponding to the isotopes of neodymium; MC-ICPMS notably detects the isotopes $^{142}$Nd, $^{143}$Nd, $^{144}$Nd$^{145}$Nd$^{146}$Nd, $^{148}$Nd, $^{150}$Nd. In the same way, the other groups comprise the curves corresponding to the isotopes of samarium, europium and gadolinium.

The invention claimed is:

1. A method for separating electrically charged species contained in a solution by an isotachophoresis method comprising:
    a first step wherein the following are introduced into the inlet of an electrophoresis capillary, in this order: a leading electrolyte with a first speed of electrophoretic migration, a solution comprising charged species with their own individual speeds of electrophoretic migration and a terminating electrolyte with a second speed of electrophoretic migration, the first speed of electrophoretic migration being the largest of the speeds of migration and the second speed being the smallest of the speeds of migration;
    the following steps are repeated until separation of at least one charged species contained in the solution is obtained:
        a second step in which a voltage is applied between the two ends of the capillary so as to start separation of the species,
        a third step in which the voltage is stopped,
        a fourth step in which a counter-pressure is applied so as to displace the species towards the inlet of the capillary, the speed of displacement of the species during application of the counter-pressure being lower than the speed of electrophoretic migration of the species under the effect of the voltage.

2. The method according to claim 1, wherein application of the counter-pressure displaces the species to the level of the inlet of the capillary.

3. The method according to claim 1, further comprising a fifth step wherein the isotopic ratios are measured by inductively coupled plasma mass spectrometry of all the species contained in the solution and separated by isotachophoresis, the mass spectrometer being directly coupled to the electrophoresis device.

4. The method according to claim 1, further comprising a fifth step wherein a first species separated prior to the third step of stopping the electric field is recovered after the second step of application of a voltage.

5. The method according to claim 4, further comprising a sixth step wherein isotopic ratios are measured by inductively coupled plasma mass spectrometry of the first species separated by isotachophoresis before continuing isotachophoresis separation of the other species, the mass spectrometer being directly coupled to the electrophoresis device.

6. The method according to claim 5, further comprising a seventh step of positioning the detectors of the inductively coupled plasma mass spectrometer on stopping the electric current.

7. The method according to claim 4, wherein the inductively coupled plasma mass spectrometer is of the multi-collection type.

8. The method according to claim 1, wherein the capillary electrophoresis device is at least partly a microfluidic system.

9. The method according to claim 1, wherein the species comprise mineral anions, mineral cations, organometallic compounds or mixtures thereof, and at least two species display isobaric interference such that the atomic mass difference between the charged species is between 0.001 and 0.9 atomic mass unit.

10. The method according to claim 1, wherein the charged species comprise transition metals, alkali metals, alkaline-earth metals, lanthanides and/or actinides.

11. The method according to claim 1, wherein the leading electrolyte and/or the terminating electrolyte is an aqueous solution of a compound comprising the elements carbon and oxygen.

* * * * *